United States Patent [19]

Schneider et al.

[11] Patent Number: 4,778,568

[45] Date of Patent: Oct. 18, 1988

[54] PROCESS FOR SEPARATING ISOMER MIXTURES OF 1,3- AND 1,4-BIS-(2-HYDROXYHEXAFLUORO-PROP-2-YL)-BENZENE

[75] Inventors: Klaus-Albert Schneider, Hattersheim am Main; Günter Siegemund, Hofheim am Taunus, both of Fed. Rep. of Germany

[73] Assignee: Hoechst Aktiengesellschaft, Frankfurt am Main, Fed. Rep. of Germany

[21] Appl. No.: 76,135

[22] Filed: Jul. 21, 1987

[30] Foreign Application Priority Data

Jul. 23, 1986 [DE] Fed. Rep. of Germany ....... 3624911

[51] Int. Cl.$^4$ ................................................ B01D 3/38
[52] U.S. Cl. ........................................ 203/29; 203/48; 203/79; 203/80; 203/96; 203/DIG. 6; 568/810; 568/811
[58] Field of Search ...................... 203/29, 48, 80, 96, 203/79, DIG. 6; 568/810, 811

[56] References Cited

U.S. PATENT DOCUMENTS

| | | | |
|---|---|---|---|
| 2,674,569 | 4/1954 | Burrage et al. | 203/96 |
| 3,236,894 | 2/1966 | England | 564/442 |
| 3,304,334 | 2/1967 | Jones | 568/811 |
| 3,879,430 | 4/1975 | O'Rear et al. | 568/811 |

FOREIGN PATENT DOCUMENTS

| | | | |
|---|---|---|---|
| 0693106 | 8/1964 | Canada | 568/810 |
| 0166634 | 8/1985 | Japan | 568/810 |

OTHER PUBLICATIONS

Sepiol, J. et al., *J. Fluorine Chem.* 24, 61–74 (1984).
Farah, B. S. et al., *J. Org. Chem.* 30, 998–1001 (1965).

*Primary Examiner*—David L. Lacey
*Assistant Examiner*—V. Manoharan

[57] ABSTRACT

Isomer mixtures of 1,3- and 1,4-bis-(2-hydroxyhexafluoroprop-2-yl)-benzene are separated by a steam distillation in the presence of $CS_2$. On cooling of the steam distillate, a solid precipitates which is composed mainly of the 1,4-isomer. After the solid has been separated off, an aqueous-organic liquid-phase mixture remains, the organic phase of which mainly contains the 1,3-isomer. The pure isomers are obtained by recrystallization or distillation respectively. These are mainly intermediates in the polymer field.

5 Claims, No Drawings

PROCESS FOR SEPARATING ISOMER MIXTURES OF 1,3- AND 1,4-BIS-(2-HYDROXYHEXAFLUORO-PROP-2-YL)-BENZENE 1,3- and 1,4-bis-(2-hydroxyhexafluoroprop-2-yl)-benzene are the compounds of the following formulae (I) and (II):

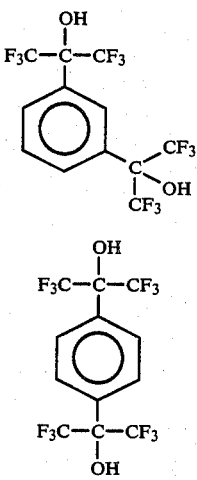

They are mainly intermediates in the polymer field. For example, by polycondensation with epichlorohydrin

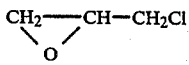

valuable epoxide resins of high chemical and thermal stability are obtained.

(I) and (II) are mainly prepared by reacting benzene with hexafluoroacetone in a molar ratio of about 1:2 in the presence of $AlCl_3$ as the catalyst; cf., for example, B. S. Farah et al., J. Org. Chem., volume 30 (1965), pages 998–1001, and J. Sepiol et al., Journal of Fluorine Chemistry, 24 (1984), pages 61–74.

In this preparation process, mixtures of (I) and (II) are formed, as shown by the two literature references, but the proportion of (I) considerably exceeds that of (II) (about 85–90% of (I) and about 15 to 10% (II)).

According to the abovementioned literature references and according to our own measurements, the melting and boiling points of (I) and (II) are:

|  | I | II |
|---|---|---|
| Melting point | (liquid at room temperature) | 85–86° C. |
| Boiling point | 209° C./760 mm Hg | — |
|  | 99° C./20 mm Hg |  |
|  | 107–112° C./24–25 mm Hg | 102–105° C./11 mm Hg |

Although the melting and boiling points of the two isomers differ, a separation by fractional crystallization is rather difficult, because of the extensive formation of mixed crystals. (I) and (II) can be separated by careful and repeated fractional distillation, but considerable losses of substances must then be accepted.

The literature reference B. S. Farah et al. (loc. cit.) does not contain any data on the separation of the two isomers in question. According to the literature reference by J. Sepiol et al. (loc. cit.), only a partial enrichment takes place in fractional distillation (Experimental—part a on pages 67/68), or by extraction of the reaction mixture, to which water has been added, with chloroform, working up of the organic phase by distillation mainly for (I) and by crystallization of (II) from the aqueous phase in the course of several days (". . . deposited after several days a crystalline substance"—see Experiment—part b on pages 68/69).

Mainly because of the long crystallization period, however, the last-mentioned separation process is hardly suitable, especially for industrial purposes.

In an endeavor to provide an improved process for separating isomer mixtures of (I) and (II), it has now been found that this object is achieved by subjecting the isomer mixtures to a steam distillation in the presence of carbon disulfide $CS_2$, separating off the solid which precipitates on cooling of the distillate and is composed mainly of the 1,4-isomer (II), likewise separating off the organic liquid phase, composed mainly of the 1,3-isomer (I), from the remaining aqueous-organic liquid-phase mixture and recovering the 1,3-isomer (I) from the organic phase.

When the steam distillate is cooled, the solid, composed mainly of (II), here precipitates immediately. The disadvantage of the long crystallization times, such as are required in the processes of J. Sepiol et al, (loc. cit.), thus does not arise in the process according to the invention. Moreover, the invention achieves a high separation effect with only slight losses of substance. The process is therefore highly economical and also very suitable for industrial application.

Separation of mixtures of (I) and (II) by a steam distillation in the presence of $CS_2$ was very surprising, because we found that the isomers can be separated only very incompletely or not at all by a steam distillation in the absence of $CS_2$ and/or in the presence of other substances.

Although $CS_2$ has been described in the literature reference B. S. Farah et al. (loc. cit.) as a suitable solvent for the reaction of, inter alia, benzene with hexafluoroacetone in the presence of $AlCl_3$ as a catalyst (cf. page 1001, right-hand column, paragraph 2), the literature reference does not give any indication of a possible role of this solvent in the separation of (I) and (II).

In principle, mixtures of (I) and (II) of any possible compositions can be separated by the process according to the invention; however, preferred starting isomer mixtures are those of about 10–90% of (I) and about 90–10% of (II), especially those of about 80–90% of (I) and about 20–10% of (II). Mixtures such as normally obtained in the reaction of benzene with hexafluoroacetone in a molar ratio of about 1:2 in the presence of $AlCl_3$ as a catalyst also fall within the scope of the particularly preferred starting isomer mixtures.

The isomer separation according to the invention succeeds even in the presence of relatively small quantities of $CS_2$. Preferably, however, the separation is carried out in the presence of about 2.0 to 6.5 mol of $CS_2$/mol of isomer mixture. The $CS_2$ can already be used as the solvent in the reaction of benzene with hexafluoroacetone and can be left in for the subsequent steam distillation according to the invention, or it may also be added to the isomer mixture just before the steam distillation according to the invention.

The steam distillation is carried out in the conventional manner, advantageously until the entire starting isomer mixture has distilled over.

When the steam distillate is cooled, a solid normally precipitates immediately, and this is separated—advantageously filtered off without or with suction—from the remaining aqueous-organic liquid-phase mixture. The solid is composed mainly of the 1,4-isomer (II); the degree of purity is in most cases between about 95 and 98%. The purity can be increased to more than 99%, for example by recrystallization say from cyclohexane.

The aqueous-organic liquid-phase mixture which has been separated from the precipitated solid is then in turn separated into the aqueous and organic phases. For complete removal of the organic constituents, the aqueous phase, can, if desired, also be extracted with inert organic solvents, for example with aliphatic halogenated hydrocarbons ($CH_2Cl_2$, $CHCl_3$, $CCl_4$, $ClCH_2$—$CH_2Cl$ and the like). The organic phases are combined and worked up in the usual way—appropriately by distillation. The 1,3-isomer (I) is thus obtained in high purity, more than 99% in the case of careful distillation.

Example (A) which follows is intended to explain the separation process according to the invention in more detail. This example is then followed by some comparison examples (B), which show that the isomer separation by steam distillation succeeds only very incompletely or not at all in the absence of $CS_2$ or even in the presence of other substances ($CH_2Cl_2$, $CHCl_3$, $CCl_4$, nitrobenzene or nitromethane).

(A) EXAMPLE

(a) Preparation of an isomer mixture of 1,3- and 1,4-bis(2-hydroxyhexafluoroprop-2-yl)-benzene (not part of the invention)

3650 g (22 mol) of hexafluoroacetone were introduced into a solution of 780 g (10 mol) of benzene in 3500 ml of carbon disulfide. The reaction was started with $AlCl_3$ and maintained at a temperature of about 30°–46° C. A total of 406 g of $AlCl_3$ was consumed. The outlet from the apparatus was closed by two "bubble counters" of 1 meter in height and filled with paraffin, and by a $CaCl_2$ tower. After the end of the reaction, the mixture was stirred for a further 12 hours and then hydrolyzed at 0°–10° C. with ice water.

The isomer ratio I:II in the hydrolyzed product was 86:14 (according to gas chromatography).

(b) Isomer separation according to the invention

The hydrolyzed batch from (a) was steam-distilled. The solid precipitating on cooling of the distillate was separated off by filtration with suction (640 g=16% crude yield relative to benzene). After recrystallization from cyclohexane, 432 g of the 1,4-isomer having a melting point of 91°–94° C. were obtained (11% yield). The organic phase of the aqueous-organic filtrate obtained after the filtration with suction was separated off, and the aqueous phase was extracted 3 times with $CH_2Cl_2$. After the combined organic phases had been dried over $MgSO_4$, the solvent was stripped off in a rotary evaporator, and the crude product thus obtained was subjected to a coarse distillation (≧100° C./25 mm Hg) through a short Vigreux column 15 (25 cm). The crude product thus prepurified (2655 g 65% yield) contained 3% of the 1,4-isomer and 96–97% of the 1,3-isomer.

By fractional vacuum distillation through a column of 140 cm length, packed with 4 mm Raschig rings, the 1,3-isomer was obtained with a purity of >99% according to gas chromatography (2301 g≙56% yield).

The spectroscopic and physical data agree with those quoted in the literature.

(B) COMPARATIVE EXAMPLES

(a) Preparation of an isomer mixture of 1,3- and 1,4-bis-(2-hydroxyhexafluoroprop-2-yl)-benzene 2.2 mol of hexafluoroacetone (365 g) were introduced into 1 mol of benzene (78 g) without a further solvent or as a mixture with 200 ml of one of the solvents contained in the table which follows. The reaction was started by addition of $AlCl_3$ and maintained at 30°–46° C. A total of 41 g of $AlCl_3$ was added. The outlet from the apparatus was closed by two "bubble counters" of 1 m in height and filled with paraffin, and by a $CaCl_2$ tower. After the end of the reaction, the mixture was stirred for a further 12 hours and then hydrolyzed at 0°–10° C. with ice water.

(b) Attempt at isomer separation

The hydrolyzed batch from (a) was steam-distilled. A solid precipitating on cooling of the distillate was separated off by filtration with suction and dried. The organic phase of the aqueous-organic filtrate obtained after the filtration with suction was separated off, and the aqueous phase was extracted 3 times with $CH_2Cl_2$. After the combined organic phases had been dried over $MgSO_4$, the $CH_2Cl_2$ and the solvent were stripped off in a rotary evaporator and the liquid crude product thus obtained was subjected to a coarse distillation (≧100° C./25 mm Hg) through a short Vigreux column (25 cm).

The stages (a) and (b) were carried out under the following conditions, with the following results:

| Solvent | Total yield of isomer mixture | Yield of isolated 1,4-isomer after steam distillation |
| --- | --- | --- |
| 1. without solvent | 57% | no separation |
| 2. nitromethane | traces | — |
| 3. 1,2-dichloroethane | 59% | 4% |
| 4. methylene chloride | 31% | 3% |

Independently of the solvent, the 1,3-/1,4-isomer ratio in the distilled product was 86:14 as in the crude product before the steam distillation.

We claim:

1. A process for separating an isomer mixture containing about 10–90% of a 1,3-isomer, 1,3-bis-(2-hydroxyhexafluoroprop-2-yl)-benzene, which is liquid at room temperature, and about 90–10% of a 1,4-isomer, 1,4-bis-(2-hydroxyhexafluoroprop-2-yl)-benzene, which is solid at room temperature, which process comprises subjecting the mixture to a steam distillation in the presence of about 2 to 6.5 mol of carbon disulfide per mol of the isomer mixture, separating off a 1,4-isomer-containing solid which precipitates on cooling of a distillate, and separating off an organic liquid phase, comprising the 1,3-isomer, from an aqueous-organic liquid-phase mixture produced by the steam distillation, and recovering the 1,3-isomer from said organic liquid phase.

2. The process as claimed in claim 1, wherein the isomer mixture used has been obtained in the reaction of benzene with hexafluoroacetone in a molar ratio of about 1:2 in the presence of AlCl₃ as a catalyst.

3. The process as claimed in claim 1, wherein the 1,4-isomer, essentially free of the 1,3-isomer, is obtained by recrystallization from the 1,4-isomer-containing solid which precipitates from the distillate.

4. The process as claimed in claim 1, wherein the 1,3-isomer, essentially free of the 1,4-isomer, is obtained by distillation of the organic liquid phase.

5. The process as claimed in claim 1, wherein the starting isomer mixture contains about 80–90% of the 1,3-isomer and about 20–10% of the 1,4-isomer.

* * * * *